United States Patent
Gonda et al.

(10) Patent No.: US 8,674,079 B2
(45) Date of Patent: Mar. 18, 2014

(54) CANCER CELL MIGRATION AND CANCER CELL INVASION INHIBITOR

(75) Inventors: Kohsuke Gonda, Sendai (JP); Hideo Higuchi, Sendai (JP); Noriaki Ohuchi, Sendai (JP); Motohiro Takeda, Sendai (JP)

(73) Assignee: Tohoku University, Sendai-shi, Miyagi (JP)

( * ) Notice: Subject to any disclaimer, the term of this patent is extended or adjusted under 35 U.S.C. 154(b) by 337 days.

(21) Appl. No.: 12/934,133

(22) PCT Filed: Mar. 19, 2009

(86) PCT No.: PCT/JP2009/055479
§ 371 (c)(1),
(2), (4) Date: Nov. 30, 2010

(87) PCT Pub. No.: WO2009/119455
PCT Pub. Date: Oct. 1, 2009

(65) Prior Publication Data
US 2011/0070163 A1     Mar. 24, 2011

(30) Foreign Application Priority Data
Mar. 27, 2008  (JP) ................................ 2008-083588

(51) Int. Cl.
*C07K 16/00*     (2006.01)

(52) U.S. Cl.
USPC ...................... 530/388.1; 424/130.1; 435/7.1

(58) Field of Classification Search
None
See application file for complete search history.

(56) References Cited

U.S. PATENT DOCUMENTS

2004/0220110 A1*  11/2004  Schmaier et al. ............... 514/17

FOREIGN PATENT DOCUMENTS

| JP | 2002-010784 | 1/2002 |
|---|---|---|
| WO | WO 98/10287 A1 | 3/1998 |
| WO | WO 00/08150 A1 | 2/2000 |
| WO | WO 2008/011107 A2 | 1/2008 |

OTHER PUBLICATIONS

Campbell, General Properties and Applications of Monoclonal Antibodies, pp. 1-32, in Monoclonal Antibody Technology, 1984, Elsevier Science Publishers.*
Katerina Oikonomopoulou et al., "Kallikrein-mediated cell signaling: targeting proteinase-activated receptors (PARs)", Biological Chemistry, Jun. 2006, vol. 387, pp. 817-824.
Stacy Seeley et al., "Structural Basis for Thrombin Activation of a Protease-Activated Receptor: Inhibition of Intramolecular Liganding", Chemistry & Biology, Nov. 2003, vol. 10, No. 11, pp. 1033-1041.
Kohsuke Gonda et al., "In Vivo Nano-imaging of Membrane Dynamics in Metastatic Tumor Cells Using Quantum Dots", Journal of Biological Chemistry, Jan. 22, 2010, vol. 285, No. 4, pp. 2750-2757.
Supplemental European Search Report (Application No. EP 09 72 6307) mailed Aug. 10, 2011.
Lawrence F. Brass et al. "Changes in the Structure and Function of the Human Thrombin Receptor during Receptor Activation, Internalization, and Recycling", The Journal of Biological Chemistry, Jan. 28, 1994, vol. 269, No. 4, pp. 2943-2952.
Adrienne Boire et al. "PAR1 is a Matrix Metalloprotease-1 Receptor that Promotes Invasion and Tumorigenesis of Breast Cancer Cells", Cell, Feb. 11, 2005, vol. 120, No. 3, pp. 303-313.
Lidija Covic et al. "Pepducin-based intervention of Thrombin-Receptor Signaling and Systemic Platelet Activation", Nature Medicine, Oct. 2002, vol. 8, No. 10, pp. 1161-1165.
The International Preliminary Report on Patentability; Application No. PCT/JP2009/055479; mailed Dec. 2, 2010.
K. Yamada et al. "Monoclonal Antibody and Synthetic Peptide Inhibitors of Human Tumor Cell Migration", Cancer Research, 1990, vol. 50, pp. 4485-4496.
Japanese Office Action (Application No. 2010-505602) mailed May 28, 2013.
Japanese Office Action dated Aug. 20, 2013, issued in the corresponding Japanese Patent Application No. 2010-505602.

* cited by examiner

*Primary Examiner* — Mark Halvorson
(74) *Attorney, Agent, or Firm* — Nixon Peabody LLP; Jeffrey L. Costellia

(57) ABSTRACT

Provided are an antibody which binds specifically PAR1 (protease activated receptor 1) or a fragment of the antibody which retains similar characteristics thereto; a composition containing the same for inhibiting the migration activity and invasion activity of cancer cells; and a medicinal composition for treating cancer and the like.

12 Claims, 4 Drawing Sheets

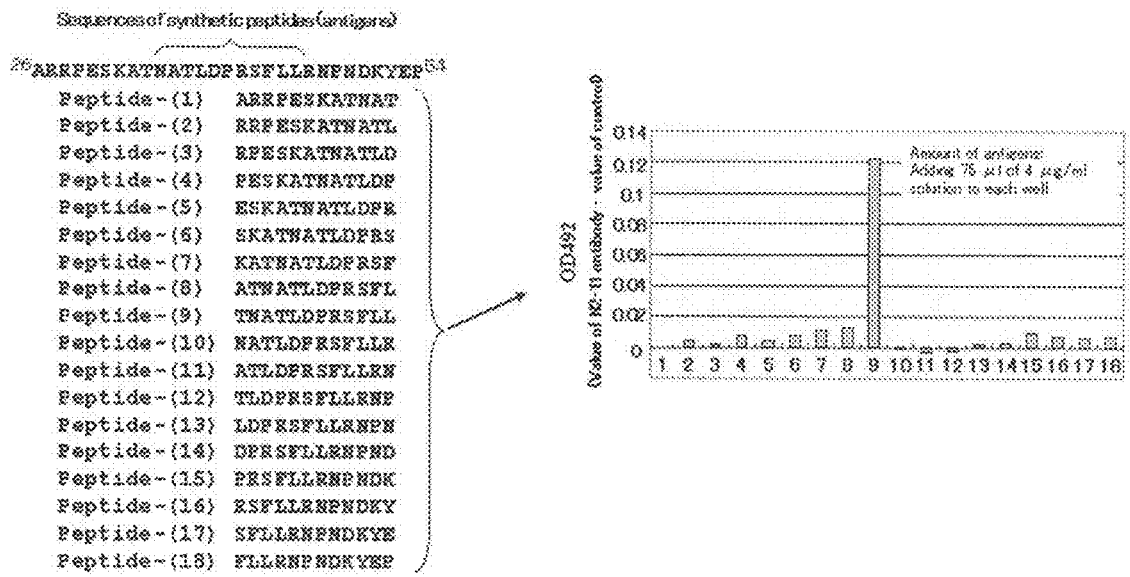
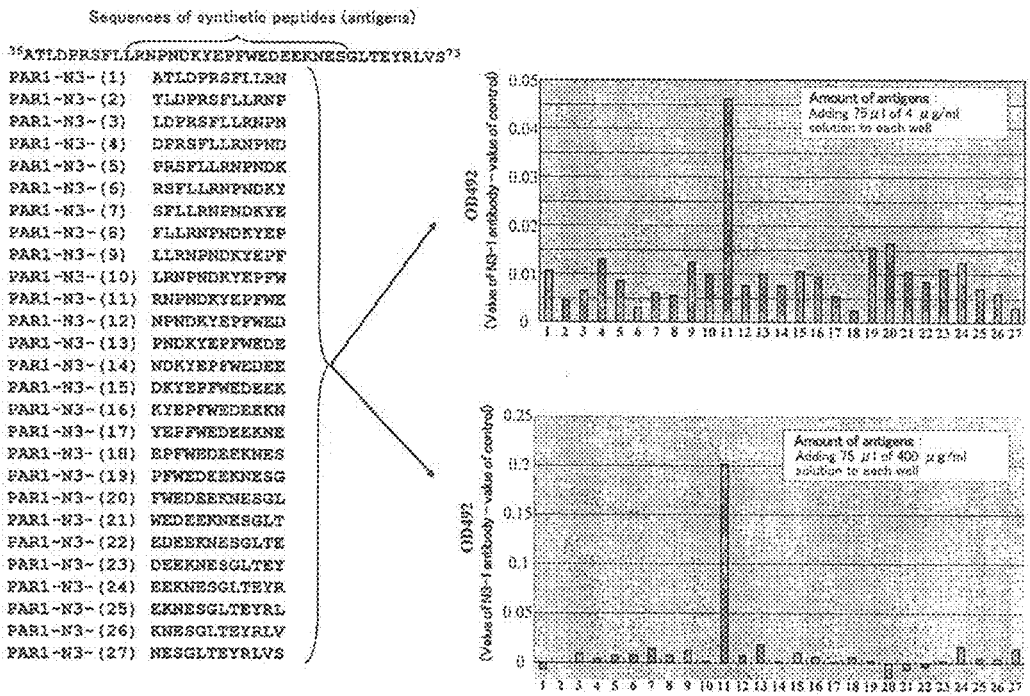

Fig. 3 Effects of PAR1 antibodies against cell
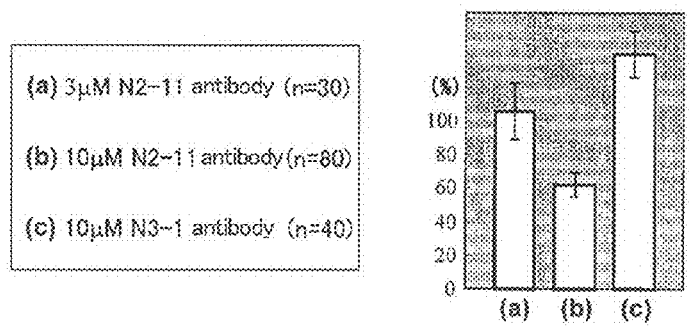
Fig. 4 Characteristics of PAR1 antibody
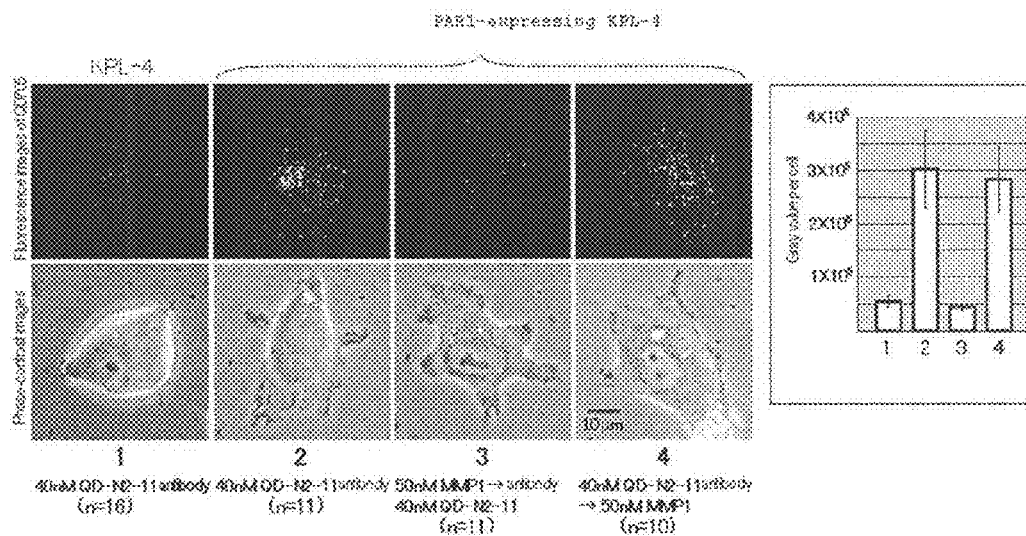

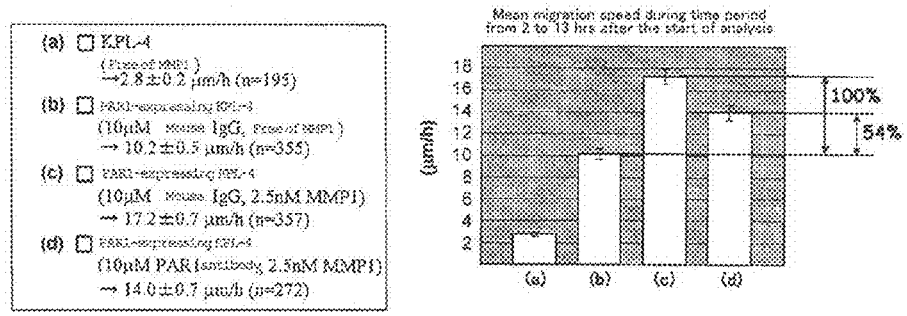
Fig. 5 Effects of PAR1 antibody against cell motion ability
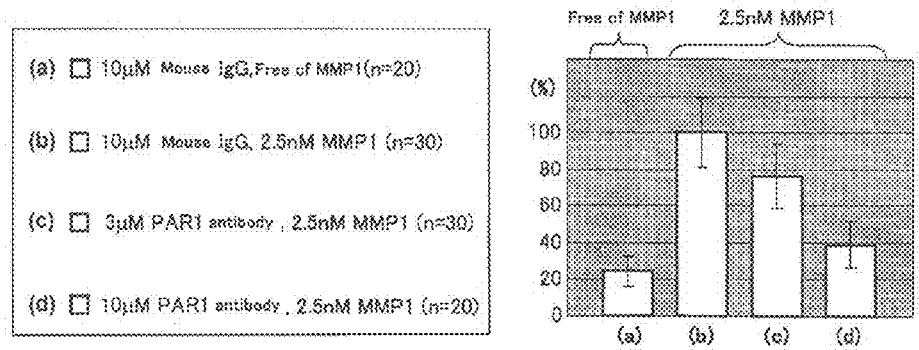
Fig. 6 Effects of PAR1 antibody against cell infiltration ability Fig. 7 Images of living tumor tissue imaged using PAR1 antibody-OD
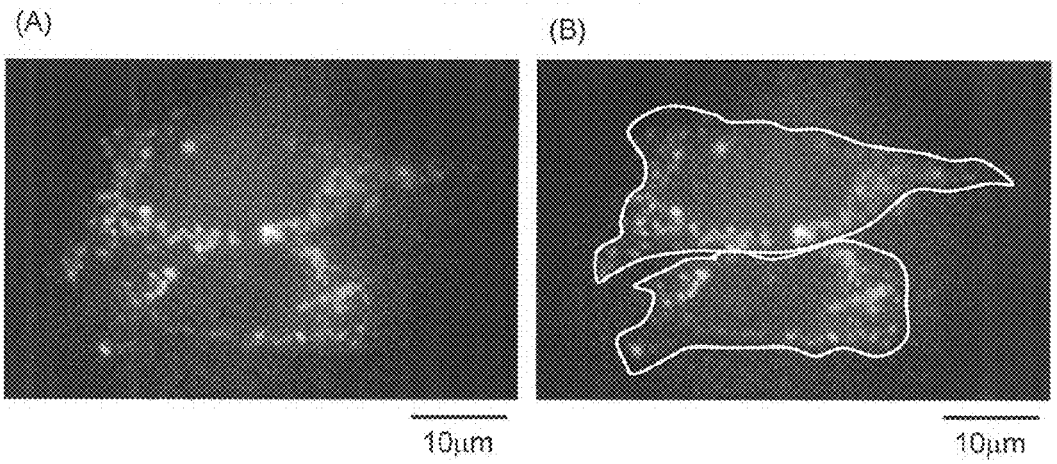
Fig. 8 Effects of polyclonal PAR1 antibody against cell infiltration ability
(a) 300nM Rabbit IgG, 2.5nM MMP1 (n=40)
(b) 100nM Polyclonal PAR1 antibody, 2.5nM MMP1 (n=40)
(c) 300nM Polyclonal PAR1 antibody, 2.5nM MMP1 (n=40)
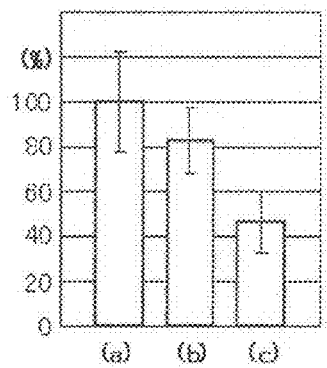

CANCER CELL MIGRATION AND CANCER CELL INVASION INHIBITOR

TECHNICAL FIELD

The present invention relates to cancer cell migration and cancer cell invasion inhibitors. More specifically, the present invention relates to a PAR1 antibody inhibiting a cell migration activity and a cell invasion activity induced by MMP1 as well as a medicinal composition containing the PAR1 antibody and the like. The present application claims priority based on Japanese Patent Application No. 2008-83588, the disclosure of which is incorporated by reference herein.

BACKGROUND ART

A typical disease resulting from abnormally elevated migration ability and invasion ability of cells is cancers. Metastasis is mentioned as one of the largest threat of cancers. Metastatic cancer cells migrate from a primary tumor through a blood vessel by cell migration, invade within the blood vessel, and then metastasize to other tissues through the blood stream. PAR1 (protease activated receptor 1) is a seven-transmembrane receptor which activates the migration ability and invasion ability of cancer cells, and is involved in the metastasis of a great variety of cancers (breast cancer, lung cancer, pancreas cancer, prostate cancer, etc.). It is known that, in the breast cancer in particular, PAR1 is expressed in most of cultured cancer cell lines having a metastatic ability, and that PAR1 is activated when the N-terminal extracellular domain (between $R_{41}$ and $S_{42}$) of the PAR1 is cleaved by a protease inherent to cancers (MMP1: matrix metalloprotease 1). The stimulation of PAR1 activation activates G protein coupled to an intracellular domain of the PAR1. It is thought that an intracellular $Ca^{2+}$ concentration is locally elevated as a result of the activation of the G protein, and the cell migration ability and cell invasion ability are enhanced by the Ca signal (see Non-Patent Document 1).

PAR1 was originally discovered as a thrombin-dependent receptor (thrombin receptor) necessary for activating platelets. Thrombin recognizes and cleaves the same site in the PAR1 as in the case of the MMP1. Also, activation of the thrombin receptor in platelets activates the $Ca^{2+}$ signal in a manner similar to that in the case of cancer cells. Currently, some monoclonal antibodies to an N-terminal cell domain of the PAR1 are marketed, which antibodies inhibit the activation of platelets. However, there is no report as to the relationship between these antibodies and the migration and invasion of cancer cells.

Even more, there is no report describing that the migration and invasion of cancer cells were inhibited by a PAR1 antibody, or that a PAR1 antibody was used for a cancer treatment.

Also, a substance named Pepducin was prepared by synthesizing a peptide corresponding to a G protein binding site of the PAR1 and modifying the peptide so as to have membrane permeability (see Non-Patent Document 2). Covic et al. succeeded in inhibiting the activity of the PAR1 by utilizing Pepducin as a G protein antagonist (inhibiting effect of Pepducin is 3 to 4 µM). On the other hand, a method applying an antibody as an anti-cancer drug is expected to show not only an effect inhibiting an activity of a target molecule but also an effect exerting an antibody-dependent cell impairing activity by immune system cells. In addition, a technique for preparing antibodies having a high affinity by genetic engineering has been established, and the safety of antibodies to a living body has been ensured. For the reasons as described above, there is a very large merit in applying antibodies as an anti-cancer drug. Accordingly, it is thought that the application of a PAR1 antibody as an anti-cancer drug has a possibility that the antibody becomes a more effective anti-cancer drug than Pepducin.

An antibody in which the epitope is a sequence from fifty-second Tyr to fifty-sixth Trp in the PAR1 was prepared by a phage display method, which antibody inhibits an activity of thrombin cleaving the PAR1. With respect to the inhibition of the cleaving activity of the PAR1 by the antibody (binding to PAR1), in particular, it is thought that the inclusion of fifty-sixth Trp in the epitope is important (see Patent Document 1). Currently, there is no report describing that the migration and invasion of cancer cells were inhibited by a PAR1 antibody, or that other peptide sequence was found as an epitope for the PAR1 antibody effective for an inhibitory effect.

Patent Document 1: JP-2002-10784 A Non-Patent Document 1: Boire A, Covic L, Agarwal A, Jacques S, Sherifi S, Kuliopulos A, PAR1 is a matrix matalloprotease-1 receptor that promotes invasion and tumorigenesis of breast cancer cells. Cell 120: 303-313 (2005)

Non-Patent Document 2: Covic L, Misra M, Bader Singh C, Kuliopulus A, Pepducin-based intervention of thrombin-receptor signaling and systematic platelet activation. Nat. Med. 8; 1161-1165 (2002)

DISCLOSURE OF THE INVENTION

Problem to be Solved by the Invention

The object of the present invention is to provide an agent effectively inhibiting a function relating to cell migration and cell invasion, and more specifically an agent effectively inhibiting a function relating to cell migration and cell invasion by suppressing an activity of PAR1 in cells.

Means for Solving the Problems

The present inventors have intensively studied so as to solve the above problems and found antibodies which bind specifically to a region containing a cleavage site in PAR1 (between $Arg_{41}$ and $Ser_{42}$) cleaved by MMP1. They have also found that the antibodies inhibit a cell migration activity and a cell invasion activity induced by MMP1, and thus the present invention has been completed.

Thus, the present invention provides:

(1) An antibody which binds specifically to PAR1 (protease activated receptor 1) to inhibit cleavage by MMP1 (matrix metalloprotease 1) and also inhibit a migration activity and an invasion activity of cancer cells, or a fragment of the antibody which retains similar characteristics thereto;

(2) The antibody according to (1), which binds specifically to a region containing a cleavage site in PAR1 (protease activated receptor 1) (between $Arg_{41}$ and $Ser_{42}$) cleaved by MMP1 (matrix metalloprotease 1), as an epitope, and inhibits the migration activity and invasion activity of cancer cells, or a fragment of the antibody which retains similar characteristics thereto;

(3) The antibody according to (2), wherein the amino acid sequence of the epitope is shown in SEQ ID NO: 1, or a fragment of the antibody which retains similar characteristics thereto;

(4) The antibody according to (3), which is a monoclonal antibody produced by a hybridoma having an accession number of FERM BP-11105 assigned by International Patent Organism Depository, National Institute of Advanced Industrial Science and Technology, or a fragment of the antibody which retains similar characteristics thereto;

(5) The antibody according to any one of (1) to (4), which is chimeric or humanized, or a fragment of the antibody which retains similar characteristics thereto;

(6) The antibody according to any one of (1) to (5), which is a monoclonal antibody;

(7) The antibody according to any one of (1) to (3) or (5), which is a polyclonal antibody;

(8) A composition for inhibiting a migration activity and an invasion activity of cancer cells, comprising the antibody or fragment according to any one of (1) to (7);

(9) A medicinal composition for treating cancers, comprising the antibody or fragment according to any one of (1) to (7);

(10) A method for treating cancers, which comprises administering an effective amount of a medicinal composition containing the antibody or fragment according to any one of (1) to (7) to a subject in need of such treatment;

(11) Use of the antibody or fragment according to any one of (1) to (7) in the production of a medicine for treating cancers;

(12) A method for imaging tumor cells or a method for detecting a tumor in a sample, which comprises bringing the antibody or fragment according to any one of (1) to (7) into contact with a sample obtained from a subject to bind it to tumor cells in the sample;

(13) An imaging agent for tumor cells, comprising the antibody or fragment according to any one of (1) to (7);

(14) A method for diagnosing a tumor, which comprises administering the antibody or fragment according to any one of (1) to (7) to a subject to investigate the binding the antibody or antibody fragment of the present invention to a tumor tissue in the body;

(15) A peptide consisting of the amino acid sequence as shown in SEQ ID NO: 1;

(16) An antigenic peptide comprising a peptide consisting of the amino acid sequence as shown in SEQ ID NO: 1 and a carrier protein;

(17) A method for preparing an antibody which binds specifically to PAR1 to inhibit cleavage by MMP1, or a fragment of the antibody which retains similar characteristics thereto, wherein said method comprises using the peptide according to (15) or the antigenic peptide according to (16);

(18) A method for purifying an antibody which binds specifically to PAR1 to inhibit cleavage by MMP1, or a fragment of the antibody which retains similar characteristics thereto, wherein said method comprises using the peptide according to (15) or the antigenic peptide according to (16); and

(19) A composition for inhibiting a migration activity and an invasion activity of cancer cells, comprising the peptide according to (15) or the antigenic peptide according to (16).

Effects of the Invention

The antibodies of the present invention which bind specifically to PAR1 to inhibit cleavage by MMP1 and also inhibit a migration activity and an invasion activity of cancer cells (hereinafter referred to as "PAR1 antibody" in the present description) can effectively inhibit the migration ability and invasion ability of cancer cells, and therefore, an excellent anti-cancer drug can be obtained. Also, it is possible to carry out detection and imaging of a tumor using the PAR1 antibodies of the present invention. Furthermore, it is possible to obtain or purify an effective PAR1 antibody using the antigenic peptide of the present invention.

BRIEF DESCRIPTION OF THE DRAWINGS

FIG. 1 is a graph showing a partial amino acid sequence of PAR1 in Example 2 (SEQ ID NO: 3) and amino acid sequences of synthetic peptides (1) to (18) in Example 2 (SEQ ID NO: 4 to 21) as well as a graph indicating the binding of N2-11 antibody to each sequence. The concentration of the peptide solution is 4 μg/ml.

FIG. 2 is a graph showing a partial amino acid sequence of PAR1 in Example 3 (SEQ ID NO: 24) and amino acid sequences of synthetic peptides PAR1-N3 (1) to (27) in Example 3 (SEQ ID NOs: 25 to 51) as well as graphs indicating the binding of N3-1 antibody to each sequence. The concentration of the peptide solution is 4 μg/ml in the upper graph, and 400 μg/ml in the lower graph.

FIG. 3 is a graph showing the percentages of the invasive cell number under conditions (a) to (c) with setting the invasive cell number under 3 μM or 10 μM mouse IgG (control) as 100%. Condition (a) shows a 3 μM N2-11 antibody (n=30) treatment, condition (b) a 10 μM N2-11 antibody (n=80) treatment, and condition (c) a 10 μM N3-1 antibody (n=40) treatment. Cells were applied to matrigel chambers at $1.5 \times 10^5$ cells/well. Under 10 μM mouse IgG, about $2.4 \times 10^3$ cells show the invasion ability. The error bar shows the standard error.

FIG. 4 is a graph showing cells obtained by (A) to (D) in Example 5 (columns 1 to 4, respectively) and quantitative analysis results of data of columns 1 to 4. The error bar shows the standard error, in which n=16 in (column 1), n=11 in (column 2), n=11 in (column 3), and n 10 in (column 4).

FIG. 5 is a graph showing mean migration speeds per hour between 2 hours and 13 hours after starting observation under conditions (a) to (d) in Table 1. The error bar shows the standard error.

FIG. 6 is a graph showing the percentages of the invasive cell number under conditions (a), (c) and (d) in Table 2 with setting the invasive cell number under condition (b) in Table 2 as 100%. Cells were applied to matrigel chambers at $1.5 \times 10^5$ cells/well, Under condition (b), about $2.2 \times 10^3$ cells show the invasion ability. The error bar shows the standard error.

FIG. 7 is a graph showing images of living tumor tissues imaged using the N2-11 antibody-QD. FIG. 7(B) shows an image of two tumor cells in FIG. 7(A) (the outline of the cells is shown with a white line). The black portions around the center of the cells show nuclei.

FIG. 8 is a graph showing the percentages of the invasive cell number under conditions (a), (b) and (c) in Table 3 with setting the invasive cell number under condition (a) in Table 3 as 100%. Cells were applied to matrigel chambers at $1.5 \times 10^5$ cells/well. Under condition (a), about $1.5 \times 10^3$ cells show the invasion ability. The error bar shows the standard error.

BEST MODE FOR CARRYING OUT THE INVENTION

In one aspect, the present invention provides a PAR1 antibody and a fragment of the antibody which retains similar characteristics thereto. In particular, the PAR1 antibodies of the present invention may be those which bind specifically to a particular region of the PAR1 containing a site cleaved by MMP1, and consequently inhibit a migration activity and an invasion activity of cancer cells. Alternatively, the PAR1 antibodies of the present invention may be those which inhibit access of MMP1 to a MMP1 cleavage site by binding specifically to the PAR1 and producing a steric hindrance. The PAR1 antibodies of the present invention suppress the migration activity and invasion activity of cancer cells by inhibiting the cleavage of the PAR1 by MMP1 in this manner. Accordingly, the PAR1 antibodies of the present invention are useful for treating cancers. The PAR1 antibodies of the present invention may be a monoclonal antibody or a polyclonal antibody.

In the present description, the "fragment of the antibody which retains similar characteristics thereto" means a fragment in which an amino acid sequence of an epitope is identical or similar to an amino acid sequence of an epitope for the PAR1 antibodies of the present invention, and which has a migration inhibitory activity and an invasion inhibitory activity against cancer cells identical or similar to those of the PAR1 antibodies of the present invention. The "fragment" of the PAR1 antibodies of the present invention means a portion of the PAR1 antibodies of the present invention, and includes, for example, a Fab fragment and the like. In the present description, the "PAR1 antibody" includes the above fragment, unless otherwise specified.

In the present description, the "epitope" means an amino acid sequence which constitutes the peptides and antigenic peptides of the present invention or is contained in these peptides, and which is recognized and bound by the antibodies or antibody fragments of the present invention.

In particular, the epitope used in the present invention is an amino acid sequence including the cleavage site (between $Arg_{4\,1}$ and $Ser_{4\,2}$) cleaved by MMP1 and having at least several, and preferably at least 10 amino acids, but is not limited thereto. Usually, the "epitope" consists of about 5 to about 1000 amino acids. The "epitope" of the present invention includes variants thereof. For example, the variants may have an amino acid sequence accompanied with deletion, addition and substitution of one or several amino acids in the "epitope" having the above amino acid sequence, or have modification of constitutive amino acids. However, such a varied or modified "epitope" should retain inherent characteristics of the "epitope", i.e. those of being recognized and bound by the antibodies or antibody fragments of the present invention.

The "particular region" of the PAR1 is a region containing the cleavage site (between $Arg_{4\,1}$ and $Ser_{4\,2}$) of the PAR1 cleaved by MMP1. The particular region is preferably an amino acid sequence containing about 10 amino acids of both sides of the above cleavage site, and most preferably an amino acid sequence NATLDPRSFLL (SEQ ID NO: 1) containing from thirty-fifth to forty-fifth amino acids of the PAR1. Preferable the antibodies or antibody fragments of the present invention recognize the amino acid sequence as shown in SEQ ID NO: 1 as an antigen recognition site (epitope).

In the present description, amino acids are noted using one letter code and three letter code known in the art. The right lower number of an amino acid represents the position of the amino acid from the N-terminus of the amino acid sequence of the PAR1. For example, $Arg_{4\,1}$ or $R_{4\,1}$ represents the forty-first arginine from the N-terminus of the amino acid sequence of the PAR1.

Among the PAR1 antibodies of the present invention which recognize the amino acid sequence as shown in SEQ ID NO: 1 as an epitope, a preferable antibody which inhibits strongly the migration activity and invasion activity of cancer cells is a monoclonal antibody (hereinafter referred to as "N2-11 antibody" in the present description) produced by a hybridoma which was deposited with International Patent Organism Depository, National Institute of Advanced Industrial Science and Technology of Central sixth, 1-1-1 Higashi, Tsukuba, Ibaraki, JAPAN on Mar. 18, 2008 under the Budapest Treaty and which has an accession number of FERM BP-11105.

As described in the Examples, the antibodies or antibody fragments of the present invention are characterized in that they recognize amino acid sequence NATLDPRSFLL (SEQ ID NO: 1) and bind specifically thereto. Such an amino acid sequence was newly found in the present invention. An advantage of recognizing the above amino acid sequence is to inhibit effectively the cleavage by MMP1 by the fact that the antibodies or antibody fragments the present invention recognize an amino acid sequence of both sides of the cleavage site of PAR1 cleaved by MMP1. The present invention is greatly significant in respect that SEQ ID NO: 1 was selected from a number of peptides constituting candidates of the recognition site.

The PAR1 antibodies of the present invention can be prepared as described below, for example. An amino acid sequence which contains the cleavage site (between $R_{4\,1}$ and $S_{4\,2}$) of animal, preferably human PAR1 cleaved by MMP1 and has at least several, preferably at least 10 amino acids is used as a target peptide. Preferable target peptide has an amino acid sequence as shown in SEQ ID NO: 1. The target peptide may be bound to a carrier protein such as, for example, keyhole limpet hemocyanin (KLH) by a known method. An animal such as mouse can be immunized using such a conjugate as an antigen to obtain hybridomas. The resulting hybridomas are cultured, and a migration activity and an invasion activity of cancer cells are evaluated using the culture supernatants, for example, by a known method such as a matrigel assay, whereby hybridomas having a strong activity can be selected. Antibodies produced by the hybridomas may be purified and isolated by a conventional method such as, for example, affinity purification. The resulting antibodies can be analyzed for their antibody specificity and antibody effect. Also, the PAR1 antibodies of the present invention can be obtained by a combination of the above method and a chemical synthetic method of peptides known in the art. Obviously, methods for preparing the PAR1 antibodies of the present invention are not limited to the above method.

Moreover, the PAR1 antibodies of the present invention may be chimerized and humanized by conventional methods. Also, the antibodies of the present invention may be single-chain antibodies. The PAR1 antibodies of the present invention include these chimeric antibodies, humanized antibodies, and single-chain antibodies.

As described above, the PAR1 antibodies of the present invention may also be polyclonal antibodies. The polyclonal PAR1 antibodies of the present invention can be obtained by a technique known to those skilled in the art. One example is shown in Example 9.

There exist antibodies recognizing a region of PAR1 different from the above amino acid sequence, for example, an antibody described in JP-2002-10784 A and N3-1 antibody having a similar recognition site thereto. However, the N3-1 antibody has neither an invasion suppressing activity nor a migration suppressing activity against cancer cells as described in the Examples. On the other hand, the present antibodies, in particular, antibodies recognizing the amino acid sequence as shown in SEQ ID NO: 1 as an epitope (preferably N2-11 antibody) or antibody fragments (preferably fragments of N2-11 antibody) have a high invasion suppressing activity and a high migration suppressing activity against cancer cells. Accordingly, the antibodies or antibody fragments of the present invention perform excellent effects for treating cancers.

Accordingly, in another aspect, the present invention provides a composition for inhibiting a migration activity and an invasion activity of cancer cells, comprising a PAR1 antibody, preferably N2-11 antibody. The composition of the present invention can effectively act both in vitro and in vivo. In particular, a composition containing a chimerized or humanized PAR1 antibody of the present invention can effectively inhibit a migration activity and an invasion activity of human cancer cells.

In still another aspect, the present invention provides a medicinal composition for treating cancers, comprising a PAR1 antibody, preferably N2-11 antibody. When used for human, the PAR1 antibody contained in the medicinal composition of the present invention is preferably chimerized, and more preferably humanized. The medicinal composition of the present invention can be prepared in any dosage forms. The dosage forms can be selected suitably according to a site, a type and a size of a cancer in a subject, characteristics of the PAR1 antibody, body situations and health conditions of a subject and the like, and may be, for example, liquid formulations such as injection and infusion solutions, semisolid to solid formulations such as transdermal patches, ointments, creams and powders. The medicinal composition of the present invention can be administered to a subject in any administration routes. The administration routes can be selected suitably according to a site, a type and a size of a cancer in a subject, characteristics of the PAR1 antibody, body situations and health conditions of a subject and the like. For example, the medicinal composition of the present invention may be administered to a subject by injection such as intradermal injection, subcutaneous injection, muscle injection and intravenous injection, by infusion, or by topical application using transdermal patches, ointments, creams and the like. The amount of the PAR1 antibody administered by the medicinal composition of the present invention is usually 5 μg/kg to 125 mg/kg, preferably 10 μg/kg to 100 mg/kg, and more preferably 50 μg/kg to 50 mg/kg per dose, and the composition may be administered once to several times per day. The administration may be made daily, every few days, weekly to every few weeks, or monthly to every few months. The medicinal composition of the present invention may contain one or more types of PAR1 antibodies. Preferably, the medicinal composition of the present invention contains N2-11 antibody or a fragment thereof. Also, the medicinal composition of the present invention may contain other effective ingredients than the PAR1 antibody, for example, known anti-cancer drugs or other drugs.

In other aspect, the present invention provides a method for treating cancers, which comprises administering an effective amount of a medicinal composition containing a PAR1 antibody or its fragment of the present invention to a subject in need of such treatment. Also, the present invention provides use of a PAR1 antibody or its fragment of the present invention in the production of a medicine for treating cancers. A preferable PAR1 antibody in the above method and use is N2-11 antibody. The subject is preferably mammals, and most preferably human.

Tumor cells express a PAR1 protein. Accordingly, in a further aspect, the present invention provides a method for imaging tumor cells or a method for detecting a tumor in a sample, wherein said method comprises bringing an antibody or antigen fragment of the present invention which binds to the above protein into contact with a sample obtained from a subject to bind it to tumor cells in the sample. Also, the present invention provides an imaging agent for tumor cells, comprising an antibody or antigen fragment of the present invention.

Moreover, the present invention provides a method for diagnosing a tumor, which comprises administering an antibody or antigen fragment of the present invention to a subject to investigate the binding of the antibody or antigen fragment of the present invention to a tumor tissue in the body.

In these methods and in the imaging agent, it is preferable to attach a detectable label or tag to an antibody or antigen fragment of the present invention. The detectable labels or tags include, for example, enzymes such as fluorescent materials, luminescent materials, or horseradish peroxidase, specific binding substances such as biotin or avidin, or positron-emitting radionuclides used for PET, SPECT or the like, but are not limited thereto. In these methods and in the imaging agent, a preferable antibody is N2-11 antibody, and a preferable antibody fragment is a fragment of the N2-11 antibody.

In a further aspect, the present invention provides an antigenic peptide comprising a peptide consisting of the amino acid sequence as shown in SEQ ID NO: 1 and a carrier protein. As described above, antibodies or antibody fragments of the present invention can be obtained or prepared using such an antigenic peptide.

In the present description, the "carrier protein" means relatively large proteins which bind to peptides having a low molecular weight but are not recognized as an antigen. Examples of the carrier proteins include, for example, bovine serum albumin (BSA), ovalbumin (OVA), and keyhole limpet hemocyanin (KLH), but are not limited thereto. The carrier proteins can be bound to the N-terminus or C-terminus of a peptide, or to a suitable amino acid in a peptide by a known method.

In a further aspect, the present invention provides a method for preparing and a method for purifying an antibody or antibody fragment of the present invention, wherein said method comprises utilizing the specific binding of the above epitope peptide or antigenic peptide to an antibody or antibody fragment of the present invention. Preferably, the antibody or antibody fragment obtained or purified by such a method is that binding specifically to PAR1 and inhibiting cleavage by MMP1. The antibody or antibody fragment of the present invention can be purified by binding the above epitope peptide or antigenic peptide to an insoluble carrier, bringing a sample containing the antibody or antibody fragment of the present invention into contact with the carrier to generate a specific binding, and then applying a suitable elution condition.

Cancers can be treated or prevented by administering the above epitope peptide or antigenic peptide, preferably the peptide consisting of the amino acid sequence as shown in SEQ ID NO: 1, to a subject in need of cancer treatment or cancer prevention, thereby generating an antibody or antibody fragment of the present invention in the subject to inhibit a migration activity and an invasion activity of cancer cells in the subject. Accordingly, in a further aspect, the present invention provides a composition for inhibiting a migration activity and an invasion activity of cancer cells, comprising the above epitope peptide or antigenic peptide.

The present invention will be described in more detail by way of the following Examples, but is not limited thereto.

Example 1

Preparation of PAR1 Antibody (A) A sequence of both sides of the cleavage site (between $R_{41}$ and $S_{42}$) of PAR1 ($N_{35}$ATLDPRSFLL$_{45}$) (SEQ ID NO: 1), and (B) a sequence located inside the cleavage site (between $R_{41}$ and $S_{42}$) of PAR1 ($_{45}$LRNPNDKYEPF- WEDEEKKNES₆₄) (SEQ ID NO: 22) were selected as targets, and C-N₃₋₅ATLDPRSFLL₄₅ (SEQ ID NO: 2) peptide and L₄₅RNPNDKYEPFWEDEEKKNES₆₄-C (SEQ ID NO: 23) peptide were synthesized by adding C to the N-terminus of sequence (A) and to the C-terminus of sequence (B). The synthetic peptides were bound to KLH using the SH group in C, and mice were immunized using the resulting conjugates as an antigen to obtain eleven (11) hybridomas. These hybridomas were named PAR1 N2-1 to PAR1 N2-11 and PAR1 N3-1 to PAR1 N3-11, respectively. Among these hybridomas, PAR1 N2-11 which showed the highest effect in a matrigel assay using culture supernatants of the hybridomas and PAR1 N3-1 which showed a very strong binding activity to SEQ ID NO: 23 were selected and analyzed for their antibody specificity and antibody effect. The antibody produced by PAR1 N2-11 was named N2-11, and the antibody produced by PAR1 N3-1 was named N3-1. Among them, the hybridoma producing the N2-11 antibody was named "PAR1 N2-11" and deposited with International Patent Organism Depository, National Institute of Advanced Industrial Science and Technology of Central sixth, 1-1-1 Higashi, Tsukuba, Ibaraki Japan on Mar. 18, 2008 under the Budapest Treaty, and obtained an accession number of FERN BP-11105. As a result of carrying out a class determination of N2-11 antibody and N3-1 antibody, it was found that they belong to IgG 1 class.

Example 2

Example 2

Determination of Antigen Recognition Site of N2-11 Antibody

The antigen recognition site of N2-11 antibody of the present invention was determined in the following manner. On the basis of partial amino acid sequence A₂₆PRPESKATNATLDPRSFLLRNPNDKYEP₅₄ (SEQ ID NO: 3) of PAR1, eighteen (18) peptides having 12 amino acids (hereinafter referred to as "peptides (1) to (18)" in the present description) were prepared, and an epitope mapping was carried out using an ELISA method. The amino acid sequences of the peptides (1) to (18) were as follows:

| Peptide (1)  | ARRPESKATNAT | (SEQ ID NO: 4)  |
| Peptide (2)  | RRPESKATNATL | (SEQ ID NO: 5)  |
| Peptide (3)  | RPESKATNATLD | (SEQ ID NO: 6)  |
| Peptide (4)  | PESKATNATLDP | (SEQ ID NO: 7)  |
| Peptide (5)  | ESKATNATLDPR | (SEQ ID NO: 8)  |
| Peptide (6)  | SKATNATLDPRS | (SEQ ID NO: 9)  |
| Peptide (7)  | KATNATLDPRSF | (SEQ ID NO: 10) |
| Peptide (8)  | ATNATLDPRSFL | (SEQ ID NO: 11) |
| Peptide (9)  | TNATLDPRSFLL | (SEQ ID NO: 12) |
| Peptide (10) | NATLDPRSELLR | (SEQ ID NO: 13) |
| Peptide (11) | ATLDPRSFLLRN | (SEQ ID NO: 14) |
| Peptide (12) | TLDPRSFLLRNP | (SEQ ID NO: 15) |
| Peptide (13) | LDPRSFLLRNPN | (SEQ ID NO: 16) |
| Peptide (14) | DPRSFLLRNPND | (SEQ ID NO: 17) |
| Peptide (15) | PRSFLLRNPNDK | (SEQ ID NO: 18) |
| Peptide (16) | RSFLLRNPNDKY | (SEQ ID NO: 19) |
| Peptide (17) | SFLLRNPNDKYE | (SEQ ID NO: 20) |
| Peptide (18) | FLLRNPNDLYEP | (SEQ ID NO: 21) |

To a 96 well plate for ELISA, 75 µl of 4 µg/ml solution was added per well, and the plate was allowed to stand at 4° C. for 12 hours to fix peptides (1) to (18). The wells were blocked at room temperature for 1 hour using 125 µl of 1% BSA containing PBS. Subsequently, a chromogenic reaction by HRP using OPD as a substrate was carried out at room temperature for 1 hour using 100 µl of a neat culture supernatant of a hybridoma as a primary antibody, and then using 100 µl of 5000-fold diluted HRP-conjugated anti-mouse antibody (Upstate) as a secondary antibody. For the chromogenic reaction, an absorbance at 492 nm (O.D. 492 nm) was detected by a plate reader, and the reactivity of N2-11 antibody to peptides (1) to (18) was investigated. As a control, 100 µl of a medium used for cultivation of a hybridoma (10% FBS-containing RPM 1640 (GIBCO)) was used. Values obtained by subtracting an O.D. 492 nm value (about 0.05) in a control experiment from the chromogenic values obtained using the N2-11 antibody were analyzed. As a result, it was found that the antigen recognition site of the N2-11 antibody is an amino acid sequence consisting of from thirty-fifth to forty-fifth amino acids of PAR1: NATLDPRSFLL (SEQ ID NO: 1) (see FIG. 1).

The N2-11 antibody showed reactivity with peptide (9) but not with peptide (10), although peptides (9) and (10) contain an identical NATLDPRSFLL sequence (O.D. 492 value: about 0.12 for peptide (9), about 0 for peptide (10); see FIG. 1). It is thought that this is attributed to the fact that the amino group exposed at the N-terminus of NATLDPRSFLL did not show reactivity with the N2-11 antibody due to the use of sequence CN₃₋₅ATLDPRSFLL₄₅ as an antigen peptide.

Although the antibody concentration in a culture supernatant of a hybridoma was generally 0.1 to 10 µg/ml, the culture supernatant of a hybridoma contained a bovine IgG from a serum (FBS) in a medium in a concentration of 2 mg/ml in 10% FBS. Accordingly, the antibody was purified by a method using ascites of SCID mice. The "SCID mouse" is an immunodeficient mouse in which very little IgG is present in the body due to the lack of functional T-cells and B-cells. Accordingly, a high purity of N2-11 antibody can be obtained by purifying the antibody using ascites of SCID mice. The antibody of the present invention was purified as follows. Into the abdominal cavity of 8 to 10 weeks old SCID mice, 500 µl of pristine (SIGMA) was injected to cause inflammation and make an environment suitable for proliferation of a hybridoma in the abdominal cavity. After 2 weeks from the injection of pristine, hybridomas producing N2-11 antibody were injected into the abdominal cavity of the mice. Ascites was taken between 1-3 weeks after the injection of cells and centrifuged (20,000×g), and the resulting supernatant was frozen and stored as an ascites solution. The antibody was purified from the ascites solution using Protein G Sepharose FF (GE Healthcare). By subjecting the purified antibody to 10% SDS-PAGE, it was confirmed that transferrin and albumin contained in the ascites solution were not included in the N2-11 antibody. The yield of the antibody was about 200 µg per 1 ml of ascites solution.

Example 3

Determination of Antigen Recognition Site of N3-1 Antibody

The antigen recognition site of N3-1 antibody of the present invention was determined in the following manner. On the basis of partial amino acid sequence A$_{3\ 6}$TLDPRSFLLRNPWEDEEKNESGLTEYRLVS$_{7\ 3}$ (SEQ ID NO: 24) of PAR1, Twenty-seven (27) peptides having 12 amino acids (hereinafter referred to as "PAR1-N3 (1) to (27)" in the present description) were prepared, and an epitope mapping was carried out using an ELISA method. The amino acid sequences of the PAR1-N3 (1) to (27) were as follows:

```
PAR1-N3 (1)    ATLDPRSELLRN    (SEQ ID NO: 25)
PAR1-N3 (2)    TLDPRSFLLRNP    (SEQ ID NO: 26)
PAR1-N3 (3)    LDPRSFLLRNPN    (SEQ ID NO: 27)
PAR1-N3 (4)    DPRSFLLRNPND    (SEQ ID NO: 28)
PAR1-N3 (5)    PRSFLLRNPNDK    (SEQ ID NO: 29)
PAR1-N3 (6)    RSFLLRNPNDKY    (SEQ ID NO: 30)
PAR1-N3 (7)    SFLLRNPNDKYE    (SEQ ID NO: 31)
PAR1-N3 (8)    FLLRNPNDKYEP    (SEQ ID NO: 32)
PAR1-N3 (9)    LLRNPNDKYEPF    (SEQ ID NO: 33)
PAR1-N3 (10)   LRNPNDKYEPFW    (SEQ ID NO: 34)
PAR1-N3 (11)   RNPNDKYEPFWE    (SEQ ID NO: 35)
PAR1-N3 (12)   NPNDKYEPFWED    (SEQ ID NO: 36)
PAR1-N3 (13)   PNDKYEPFWEDE    (SEQ ID NO: 37)
PAR1-N3 (14)   NDKYEPFWEDEE    (SEQ ID NO: 38)
PAR1-N3 (15)   DKYEPFWEDEEK    (SEQ ID NO: 39)
PAR1-N3 (16)   KYEPFWEDEEKN    (SEQ ID NO: 40)
PAR1-N3 (17)   YEPFWEDEEKNE    (SEQ ID NO: 41)
PAR1-N3 (18)   EPFWEDEEKNES    (SEQ ID NO: 42)
PAR1-N3 (19)   PFWEDEEKNESG    (SEQ ID NO: 43)
PAR1-N3 (20)   FWEDEEKNESGL    (SEQ ID NO: 44)
PAR1-N3 (21)   WEDEEKNESGLT    (SEQ ID NO: 45)
PAR1-N3 (22)   EDEEKNESGLTE    (SEQ ID NO: 46)
PAR1-N3 (23)   DEEKNESGLTEY    (SEQ ID NO: 47)
PAR1-N3 (24)   EEKNESGLTEYR    (SEQ ID NO: 48)
PAR1-N3 (25)   EKNESGLTEYRL    (SEQ ID NO: 49)
PAR1-N3 (26)   KNESGLTEYRLV    (SEQ ID NO: 50)
PAR1-N3 (27)   NESGLTEYRLVS    (SEQ ID NO: 51)
```

The reactivity of N3-1 antibody to PAR1-N3 (1) to (27) was investigated using a method similar to that in Example 2, excepting that two solutions of 4 µg/ml and 400 µg/ml per well were used. Since an S/N ratio is somewhat poor in a 4 µg/ml peptide solution, a 400 µg/ml peptide solution was used in order to raise the S/N ratio. As a result, it was found that the antigen recognition site of the N3-1 antibody is an amino acid sequence consisting of from forty-sixth to fifty-seventh amino acids of PAR1: RNPNDKYEPFWE (SEQ ID NO: 35) (see FIG. 2). In this connection, the OD values vary depending on reaction times of the reaction using OPD as a substrate, and therefore, they show relative bindings to antigens but are not indicators showing substantial binding forces of an antibody.

The N3-1 antibody was purified using a method similar to that in Example 2. By subjecting the purified antibody to 10% SDS-PAGE, it was confirmed that transferrin and albumin contained in the ascites solution were not included in the N3-1 antibody. The yield of the antibody was about 400 µg per ml of ascites solution.

Example 4

Comparison of N2-11 Antibody and N3-1 Antibody

In order to investigate to what extent the N2-11 antibody and N3-1 antibody can inhibit a thrombin-dependent cell invasion activity, invasion-inhibiting effects of the antibodies were tested using a matrigel assay. In order to prepare cells used for the assay, firstly, a cell line stably expressing PAR1-GFP (hereinafter referred to as "PAR1-expressing KPL-4" in the present description) was prepared from low invasive breast cancer cultured cells KPL-4 (low PAR1-expressing cell line). $1.5\times10^5$ PAR1-expressing KPL-4 cells were suspended by a trypsin treatment, and washed with PBS. To the cells, 3 or 10 µM N2-11 antibody or 10 µM N3-1 antibody or 3 or 10 µM mouse IgG which is a control antibody was added, and the mixture was incubated at 37° C. for 90 minutes. The cells were then seeded on Cell Culture Insert (BD Biosciences), and cultured at 37° C. for 45 hours. As a solution of an inducing substance immerging the Insert, a 10% PBS containing 2.5 U/ml thrombin (WAKO) solution was used, and after 45 hours, invasive cells migrated to the bottom of a membrane filter was HE-stained to count the number of invasive cells. For counting the invasive cell number, random spots on the filter were scanned in a size of 0.66 mm×0.66 mm to calculate the mean cell number. Then, the percentages of the invasive cell number when treated with the N2-11 antibody and N3-1 antibody were shown in FIG. 3 with setting the invasive cell number when treated with the mouse IgG as 100%. On this occasion, the invasive cell number when treated with 10 µM mouse IgG was about $2.4\times10^3$ cells. In FIG. 3, (a) shows the percentage of the cell number when treated with 3 µM N2-11 antibody (n=30), (b) shows the percentage when treated with 10 µM N2-11 antibody (n=80), and (c) shows the percentage when treated with 10 µM N3-1 antibody (n=40).

Results

It was found that the N2-11 antibody has a 40% inhibitory effect in a 10 µM antibody concentration but the N3-1 antibody does not have such an activity (see FIG. 3 (b) and FIG. 3(c)). Thus, it is evident that an antibody recognizing a sequence containing amino acids from fifty-second Tyr to fifty-sixth Trp of PAR1 as an epitope does not inhibit the cell invasion ability.

Thus, it is believed that the N2-11 antibody is more effective than the N3-1 antibody for preparing an antibody medicine having an inhibitory effect against the cell invasion. For this reason, effects of the N2-11 antibody were investigated hereafter.

Example 5

Example 5

Investigation of Antibody Characteristics

In order to evaluate whether the N2-11 antibody can specifically recognize PAR1 on a cell surface, PAR1-expressing KPL-4 was prepared and characteristics of the N2-11 antibody to KPL-4 and PAR1-expressing KPL-4 were then investigated by the following (A) to (D):

(A) KPL-4 cells were suspended by a trypsin treatment, and washed with an FBS-free L-15 solution (GIBCO). 2 µM mouse IgG (SIGMA) containing L-15 medium was added, incubation was carried out at 37° C. for 15 minutes, blocking was carried out, 40 nM N2-11 antibody-QD probe was further added, and incubation was carried out at 37° C. for 30 minutes. Then, the N2-11 antibody-QD probe was washed with L-15 medium, 0.5% FBS containing L-15 medium was added, cells were seeded on glass bottom dishes, and observation and analysis of the cells were carried out. In this connection, the N2-11 antibody-QD probe is a probe in which the N2-11 antibody was bound to high-intensity fluorescent nanoparticles QD705 (Invitrogen).

(B) PAR1-expressing KPL-4 cells were suspended by a trypsin treatment, and washed with an PBS-free L-15 solution (GIBCO). 2 µM mouse IgG (SIGMA) containing L-15 medium was added, incubation was carried out at 37° C. for 15 minutes, blocking was carried out, 40 nM N2-11 antibody-QD probe was further added, and incubation was carried out at 37° C. for 30 minutes. Then, the N2-11 antibody-QD probe was washed with L-15 medium, 0.5% FBS containing L-15 medium was added, cells were seeded on glass bottom dishes, and observation and analysis of the cells were carried out.

(C) PAR1-expressing KPL-4 cells were suspended by a trypsin treatment, and washed with an FBS-free L-15 solution (GIBCO). 50 nM MMP1 (SIGMA) was added, and incubation was carried out at 37° C. for 60 minutes. Then, 2 µM mouse IgG (SIGMA) containing L-15 medium was added, incubation was carried out at 37° C. for 15 minutes, blocking was carried out, 40 nM N2-11 antibody-QD probe was further added, and incubation was carried out at 37° C. for 30 minutes. Then, the N2-11 antibody-QD probe was washed with L-15 medium, 0.5% FBS containing L-15 medium was added, cells were seeded on glass bottom dishes, and observation and analysis of the cells were carried out.

(D) PAR1-expressing KPL-4 cells were suspended by a trypsin treatment, and washed with an FBS-free L-15 solution (GIBCO). 2 µM mouse IgG (SIGMA) containing L-15 was added, incubation was carried out at 37° C. for 15 minutes, blocking was carried out, 40 nM N2-11 antibody-QD probe was further added, and incubation was carried out at 37° C. for 30 minutes. Then, the N2-11 antibody-QD probe was washed with L-15 medium, 50 nM MMP1 was added, and incubation was carried out at 37° C. for 60 minutes. Then, washing with L-15 medium was carried out, 0.5% FBS containing L-15 medium was added, cells were seeded on glass bottom dishes, and observation and analysis of the cells were carried out.

In addition, binding properties of the antibody were quantitatively analyzed using the N2-11 antibody-QD probe. The particle number of the above fluorescent nanoparticles and the fluorescent intensity are in a proportional relation. Fluorescence images at an exposure time of 100 ms were converted to TIFF format images in a contrast in range from 1,150 to 1,600 of SOLIS software (Andor). Subsequently, a total gray value per 1 cell derived from the N2-11 antibody-QD fluorescence was calculated by subtracting a background gray value from a total gray value (1-256 tones of gray value) of one cell with Image J software.

Results:

The cells obtained in the above (A) to (D) and the results of the quantitative analysis based on the data obtained are shown in FIG. 4. The results from (A) to (D) correspond to columns 1 to 4 in the figure, respectively. As a result of observation of the cells, it was found that the expression level of PAR1 was small in the KPL-4 cells, and therefore, the N2-11 antibody-QD only slightly reacted therewith (column 1), that "PAR1 on the cell membrane" and "PAR1 taken up in the cells" were strongly labeled in dots in the PAR1-expressing KPL-4 cells by labeling with the N2-11 antibody-QD (column 2), that PAR1 on the cell membrane was cleaved by MMP1, and therefore, the N2-11 antibody could not recognize the PAR1 and it was not labeled with the N2-11 antibody-QD (column 3), and that, when the PAR1-expressing KPL-4 cells were treated with MMP1 after labeled with the N2-11 antibody-QD, the N2-11 antibody was bound to the cells to the extent similar to that in column 2 (column 4). Also, it was found from the right panel of the quantitative analysis that the amount of the N2-11 antibody bound to the PAR1-expressing KPL-4 was about 6 times the amount bound to the KPL-4, that, when the PAR1-expressing KPL-4 was treated with 50 nM MMP1, the amount of the N2-11 antibody bound was the same level as that in KPL-4, and that, when the cells were treated with MMP1 after labeled with the N2-11 antibody, the N2-11 antibody was bound to the cells to the extent similar to that in the case not treated with MMP1.

Thus, the results show that the N2-11 antibody recognizes a sequence of PAR1 on the cell membrane, in which the cleavage site is not cleaved, and binds specifically to the sequence, and inhibits the cleavage of the PAR1 by MMP1.

Example 6

Example 6

Investigation of Effects of Antibody Against Cell Migration Ability

In PAR1-expressing KPL-4 cells, the PAR1 is activated by MMP1 treatment, and the cell invasion ability is enhanced. Accordingly, observation of flame shootings over time (time-laps) of cell migration of the PAR1-expressing KPL-4 cells and analysis of the migration trajectory were carried out to investigate whether the N2-11 antibody inhibits the MMP1-dependent cell migration ability. $7 \times 10^4$ PAR1-expressing KPL-4 cells were suspended by a trypsin treatment, and washed with PBS. To the cells, 10 µM N2-11 antibody or mouse IgG which is a control antibody was added, and the mixture was incubated at 37° C. for 60 minutes. Then, 10% FBS containing L-15 medium which contains 2.5 nM MMP1 was added, and the cells were seeded on glass bottom dishes. The images of the flame shootings over time of the cell migration were taken every two minutes, and the trajectory of the cell migration was traced. Mean migration speed per hour between 2 hours and 13 hours after starting the observation of the flame shootings over time was calculated. In the trajectory of the cell migration, the barycentric position of the nucleus was used as an indicator, and all cells capable of tracing were analyzed so that data were not biased. As a control experiment, KPL-4 cells and PAR1-expressing KPL-4 cells untreated with MMP1 were also analyzed in a similar manner.

Results:

The mean migration speeds calculated using the N2-11 antibody are shown in FIG. 5, and the calculated values are shown in Table 1.

TABLE 1

| Cells | Conditions | Calculated values |
|---|---|---|
| KPL-4 | in the absence of MMP1 | 2.8 ± 0.2 μm/h (n = 195) |
| PAR1-expressing KPL-4 | 10 μM mouse IgG (in the absence of MMP1) | 10.2 ± 0.5 μm/h (n = 355) |
| PAR1-expressing KPL-4 | 10 μM mouse IgG (in the presence of 2.5 nM MMP1) | 17.2 ± 0.7 μm/h (n = 357) |
| PAR1-expressing KPL-4 | 10 μm N2-11 antibody (in the presence of 2.5 nM MMP1) | 14.0 ± 0.7 μm/h (n = 272) |

From Table 1, it is evident that KPL-4 has the latest migration speed, and PAR1-expressing KPL-4 cells treated with 10 μM mouse IgG show an elevation of the migration speed even in the absence of MMP1. Also, PAR1-expressing KPL-4 cells treated with the mouse IgG showed a great elevation of the migration speed in the presence of 2.5 nM MMP1 as compared with that in the absence of MMP1, and the treatment with 10 μM N2-11 antibody showed suppression of the elevation of the migration speed in the presence of MMP1. When the degree of the elevation of the migration speed of the PAR1-expressing KPL-4 cells treated with the mouse IgG brought about by MMP1 (7.0 μm/h) is set as 100%, the degree of the elevation of the migration speed in the presence of the N2-11 antibody brought about by MMP1 (3.8 μm/h) was 54%.

Thus, the results show that the migration speed of the PAR1-expressing cells is elevated by MMP1 treatment, but the action of MMP1 cleaving PAR1 is inhibited by treating with the N2-11 antibody and the activation of the migration ability is inhibited by about 50%.

Example 7

Example 7

Investigation of Effects of Antibody Against Cell Invasion Ability

In PAR1-expressing KPL-4 cells, the PAR1 is activated by MMP1 treatment, and the cell invasion ability is enhanced. Accordingly, a matrigel assay of PAR1-expressing KPL-4 was carried out in the presence of the N2-11 antibody to investigate whether the N2-11 antibody inhibits the MMP1-dependent cell invasion ability. 1.5×10⁵ PAR1-expressing KPL-4 cells were suspended by a trypsin treatment, and washed with PBS. To the cells, 3 or 10 μM N2-11 antibody or mouse IgG which is a control antibody was added, and the mixture was incubated at 37° C. for 90 minutes. The cells were then seeded on Cell Culture Insert, and cultured at 37° C. for 45 hours. As a solution of an inducing substance immerging the Insert, a 10% FBS containing 2.5 nM MMP1 solution was used, and after 45 hours, invasive cells migrated to the bottom of a membrane filter was HE-stained to count the number of invasive cells. For counting the invasive cell number, random spots in the filter were scanned in a size of 0.66 mm×0.66 mm to calculate the mean cell number. Then, the percentage of the invasive cell number when treated with the N2-11 antibody was determined with setting the invasive cell number when treated with the mouse IgG as 100%.

Results:

The percentages of the invasive cell number when treated with the N2-11 antibody are shown in FIG. 6 with setting the mean invasive cell number under condition (b) as 100%, and the calculated values are shown in the following Table 2.

TABLE 2

| Conditions | Calculated values |
|---|---|
| (a) 10 μM mouse IgG (in the absence of MMP1) | 24.3 ± 8.5% (n = 20) |
| (b) 10 μM mouse IgG (in the presence of 2.5 nM MMP1) | 100 ± 18.9% (n = 20) |
| (c) 3 μM N2-11 antibody (in the presence of 2.5 nM MMP1) | 76.2 ± 17.4% (n = 30) |
| (d) 10 μM N2-11 antibody (in the presence of 2.5 nM MMP1) | 38.9 ± 12.5% (n = 20) |

Thus, the results show that the invasion ability of the PAR1-expressing cells is elevated by MMP1 treatment, but the action of MMP1 cleaving PAR1 is inhibited in a dose-dependent manner by treating with the N2-11 antibody and the activation of the invasion ability is inhibited by about 60%.

From the results of the above Examples 5 to 7, it is evident that the N2-11 antibody recognizes the cleavage site of PAR1, binds specifically thereto, and inhibits the activity of MMP1 cleaving PAR1, thereby inhibiting the MMP1-dependent cell migration activity and cell invasion activity of the PAR1-expressing cells. Thus, it is evident that the N2-11 antibody can be an antibody medicine effective for cancer treatment.

Example 8

Example 8

Investigation of Specificity of Antibody to Tumor Cells

By an original in vivo imaging method using N2-11 antibody-QD similar to that in Example 5 as a probe, a vital staining of a tumor tissue was carried out to investigate whether the antibody prepared as described above is specific to PAR1 in a tumor tissue. To SCID mice, 1×10⁶ PAR1-expressing KPL-4 cells were injected subcutaneously. The mice were then fed for 4 weeks to prepare a tumor derived from the PAR1-expressing KPL-4 cells. The tumor was exposed to prepare a small window for observation, and the N2-11 an body-QD probe was then injected via the tail vein of the mice in a blood concentration of 10 nM. Subsequently, the tumor tissue in the living mice was observed using an original imaging apparatus.

Results:

An image in which the N2-11 antibody-QD specifically reacts with tumor cells is shown in FIG. 7. From FIG. 7, it is evident that the N2-11 antibody is specific to the tumor cells in the living body of mice. Thus, the results suggest that the N2-11 antibody can inhibit the PAR1 activity of living tumor cells by increasing the concentration or binding ability (binding constant).

Example 9

Example 9

Preparation of Polyclonal PAR1 Antibody and Investigation of Activity to Tumor Cells A sequence of both sides of the cleavage site (between $R_{41}$ and $S_{42}$) of PAR1 ($N_{35}$ATLDPRSFLL$_{45}$) (SEQ ID NO:

1) was selected as a target, and (N$_3$ $_5$ATLDPRSFLL$_4$ $_5$ (SEQ ID NO: 2) peptide was synthesized by adding C to the N-terminus of the above sequence. The synthetic peptide was bound to KLH using the SH group in C, and rabbits were immunized using the resulting conjugate as an antigen to prepare an antiserum to PAR1. In order to carry out affinity purification of the antiserum, a column was then prepared using the peptide as an antigen and SulfoLink coupling gel (PIERCE). The antiserum was applied to the column, and the column was then washed with PBS (pH 7.2) of 5 times or more the column volume. Subsequently, the PAR1 polyclonal antibody was eluted using 3M MgCl$_2$. After the elution, the solution was dialyzed against PBS to obtain a purified PAR1 antibody (about 0.4 mg of a purified antibody was obtained from 10 ml of the antiserum). The cell invasion activity of the polyclonal antibody was investigated using a matrigel in a manner similar to that in the assay of the monoclonal antibody. 300 nM Rabbit IgG was used as a control.

Results:

The percentages of the invasive cell number when treated with the PAR1 polyclonal antibody are shown in FIG. 8 with setting the mean invasive cell number under condition (a) as 100%, and the calculated values are shown in Table 3 below.

TABLE 3

| Conditions | Calculated values |
| --- | --- |
| (a) 300 nM rabbit IgG (in the presence of 2.5 nM MMP1) | 100% ± 22.2% (n = 40) |
| (b) 100 nM polyclonal PAR1 antibody (in the presence of 2.5 nM MMP1) | 82.6% ± 14.3% (n = 40) |
| (c) 300 nM polyclonal PAR1 antibody (in the presence of 2.5 nM MMP1) | 46.5% ± 13.6% (n = 40) |

From Table 3, it is evident that 300 nM polyclonal PAR1 antibody inhibits the cell invasion ability of PAR1-expressing KPL-4 by about 55% when the invasive cell number under condition (a) is set as 100%.

Thus, the results show that 300 nM polyclonal PAR1 antibody has an effect suppressing the invasion ability of cancer cells in the same level as 10 μM monoclonal PAR1 antibody (inhibitory effect: about 60%). This suggests that a gene of the monoclonal PAR1 antibody can be modified by a genetic engineering technique to obtain 10 to 100-fold enhancement of the inhibitory effect, and shows that the antibody of the present invention can be used as an effective anti-cancer drug.

In addition, it is also evident from these experimental results that the antibody of the present invention can be used not only as an effective anti-cancer drug, but also in detection of a tumor.

INDUSTRIAL APPLICABILITY

According to the present invention, it is suggested that the PAR1 antibody can be an antibody medicine effective for cancer treatment because the PAR1 antibody inhibits the MMP1-dependent cell migration ability and cell invasion ability in PAR1-expressing cells and specifically reacts with tumor cells in the living body of mice. Also, the antibody of the present invention can be used for detection of a tumor and the like.

The invention claimed is:

1. A monoclonal antibody produced by a hybridoma having an accession number of FERM BP-11105 assigned by International Patent Organism Depository, National Institute of Advanced Industrial Science and Technology, or a antigen-binding antibody fragment thereof.

2. The antibody according to claim 1, wherein the antibody is chimeric or humanized, or a antigen-binding antibody fragment thereof.

3. A composition for inhibiting migration activity and invasion activity of cancer cells, comprising the antibody of claim 1 or antigen-binding antibody fragment thereof.

4. A medicinal composition for treating cancers, comprising the antibody or antigen-binding antibody fragment thereof according to claim 1.

5. A method for treating cancers, which comprises administering an effective amount of a medicinal composition containing the antibody or antigen-binding antibody fragment according to claim 1 to a subject in need of such treatment.

6. A method for imaging tumor cells or a method for detecting a tumor in a sample, which comprises bringing the antibody or antigen-binding antibody fragment according to claim 1 into contact with a sample obtained from a subject to bind it to tumor cells in the sample.

7. An imaging agent for tumor cells, comprising the antibody or a antigen-binding antibody fragment thereof according to claim 1.

8. A method for diagnosing a tumor, which comprises administering the antibody or antigen-binding antibody fragment according to claim 1 to a subject to investigate the binding of the antibody or antigen-binding antibody fragment of the present invention to a tumor tissue in the body.

9. A method for preparing an antibody produced by a hybridoma having an accession number of FERM BP-11105, wherein said method comprises using a peptide comprising the amino acid sequence as shown in SEQ ID NO: 1.

10. A method for purifying an antibody produced by a hybridoma having an accession number of FERM BP-11105, wherein said method comprises using a peptide comprising the amino acid sequence as shown in SEQ ID NO: 1.

11. A method for preparing an antibody produced by a hybridoma having an accession number of FERM BP-11105, wherein said method comprises using the antigenic peptide comprising the amino acid sequence as shown in SEQ ID NO: 1 and a carrier protein.

12. A method for purifying an antibody produced by a hybridoma having an accession number of FERM BP-11105, wherein said method comprises using the antigenic peptide comprising the amino acid sequence as shown in SEQ ID NO: 1 and a carrier protein.

\* \* \* \* \*

SEQUENCE LISTING

```
<160> NUMBER OF SEQ ID NOS: 51

<210> SEQ ID NO 1
<211> LENGTH: 11
<212> TYPE: PRT
<213> ORGANISM: Homo sapiens

<400> SEQUENCE: 1

Asn Ala Thr Leu Asp Pro Arg Ser Phe Leu Leu
1               5                   10

<210> SEQ ID NO 2
<211> LENGTH: 11
<212> TYPE: PRT
<213> ORGANISM: Artificial
<220> FEATURE:
<223> OTHER INFORMATION: PAR1 with N-terminal Cys

<400> SEQUENCE: 2

Cys Ala Thr Leu Asp Pro Arg Ser Phe Leu Leu
1               5                   10

<210> SEQ ID NO 3
<211> LENGTH: 29
<212> TYPE: PRT
<213> ORGANISM: Homo sapiens

<400> SEQUENCE: 3

Ala Pro Arg Pro Glu Ser Lys Ala Thr Asn Ala Thr Leu Asp Pro Arg
1               5                   10                  15
```

Ser Phe Leu Leu Arg Asn Pro Asn Asp Lys Tyr Glu Pro
            20                  25

<210> SEQ ID NO 4
<211> LENGTH: 12
<212> TYPE: PRT
<213> ORGANISM: Homo sapiens

<400> SEQUENCE: 4

Ala Arg Arg Pro Glu Ser Lys Ala Thr Asn Ala Thr
1               5                   10

<210> SEQ ID NO 5
<211> LENGTH: 12
<212> TYPE: PRT
<213> ORGANISM: Homo sapiens

<400> SEQUENCE: 5

Arg Arg Pro Glu Ser Lys Ala Thr Asn Ala Thr Leu
1               5                   10

<210> SEQ ID NO 6
<211> LENGTH: 12
<212> TYPE: PRT
<213> ORGANISM: Homo sapiens

<400> SEQUENCE: 6

Arg Pro Glu Ser Lys Ala Thr Asn Ala Thr Leu Asp
1               5                   10

<210> SEQ ID NO 7
<211> LENGTH: 12
<212> TYPE: PRT
<213> ORGANISM: Homo sapiens

<400> SEQUENCE: 7

Pro Glu Ser Lys Ala Thr Asn Ala Thr Leu Asp Pro
1               5                   10

<210> SEQ ID NO 8
<211> LENGTH: 12
<212> TYPE: PRT
<213> ORGANISM: Homo sapiens

<400> SEQUENCE: 8

Glu Ser Lys Ala Thr Asn Ala Thr Leu Asp Pro Arg
1               5                   10

<210> SEQ ID NO 9
<211> LENGTH: 12
<212> TYPE: PRT
<213> ORGANISM: Homo sapiens

<400> SEQUENCE: 9

Ser Lys Ala Thr Asn Ala Thr Leu Asp Pro Arg Ser
1               5                   10

<210> SEQ ID NO 10
<211> LENGTH: 12
<212> TYPE: PRT
<213> ORGANISM: Homo sapiens

<400> SEQUENCE: 10

Lys Ala Thr Asn Ala Thr Leu Asp Pro Arg Ser Phe
1               5                   10

```
<210> SEQ ID NO 11
<211> LENGTH: 12
<212> TYPE: PRT
<213> ORGANISM: Homo sapiens

<400> SEQUENCE: 11

Ala Thr Asn Ala Thr Leu Asp Pro Arg Ser Phe Leu
1               5                   10

<210> SEQ ID NO 12
<211> LENGTH: 12
<212> TYPE: PRT
<213> ORGANISM: Homo sapiens

<400> SEQUENCE: 12

Thr Asn Ala Thr Leu Asp Pro Arg Ser Phe Leu Leu
1               5                   10

<210> SEQ ID NO 13
<211> LENGTH: 12
<212> TYPE: PRT
<213> ORGANISM: Homo sapiens

<400> SEQUENCE: 13

Asn Ala Thr Leu Asp Pro Arg Ser Phe Leu Leu Arg
1               5                   10

<210> SEQ ID NO 14
<211> LENGTH: 12
<212> TYPE: PRT
<213> ORGANISM: Homo sapiens

<400> SEQUENCE: 14

Ala Thr Leu Asp Pro Arg Ser Phe Leu Leu Arg Asn
1               5                   10

<210> SEQ ID NO 15
<211> LENGTH: 12
<212> TYPE: PRT
<213> ORGANISM: Homo sapiens

<400> SEQUENCE: 15

Thr Leu Asp Pro Arg Ser Phe Leu Leu Arg Asn Pro
1               5                   10

<210> SEQ ID NO 16
<211> LENGTH: 12
<212> TYPE: PRT
<213> ORGANISM: Homo sapiens

<400> SEQUENCE: 16

Leu Asp Pro Arg Ser Phe Leu Leu Arg Asn Pro Asn
1               5                   10

<210> SEQ ID NO 17
<211> LENGTH: 12
<212> TYPE: PRT
<213> ORGANISM: Homo sapiens

<400> SEQUENCE: 17

Asp Pro Arg Ser Phe Leu Leu Arg Asn Pro Asn Asp
1               5                   10

<210> SEQ ID NO 18
<211> LENGTH: 12
```

```
<212> TYPE: PRT
<213> ORGANISM: Homo sapiens

<400> SEQUENCE: 18

Pro Arg Ser Phe Leu Leu Arg Asn Pro Asn Asp Lys
1               5                   10

<210> SEQ ID NO 19
<211> LENGTH: 12
<212> TYPE: PRT
<213> ORGANISM: Homo sapiens

<400> SEQUENCE: 19

Arg Ser Phe Leu Leu Arg Asn Pro Asn Asp Lys Tyr
1               5                   10

<210> SEQ ID NO 20
<211> LENGTH: 12
<212> TYPE: PRT
<213> ORGANISM: Homo sapiens

<400> SEQUENCE: 20

Ser Phe Leu Leu Arg Asn Pro Asn Asp Lys Tyr Glu
1               5                   10

<210> SEQ ID NO 21
<211> LENGTH: 12
<212> TYPE: PRT
<213> ORGANISM: Homo sapiens

<400> SEQUENCE: 21

Phe Leu Leu Arg Asn Pro Asn Asp Leu Tyr Glu Pro
1               5                   10

<210> SEQ ID NO 22
<211> LENGTH: 21
<212> TYPE: PRT
<213> ORGANISM: Homo sapiens

<400> SEQUENCE: 22

Leu Arg Asn Pro Asn Asp Lys Tyr Glu Pro Phe Trp Glu Asp Glu Glu
1               5                   10                  15

Lys Lys Asn Glu Ser
            20

<210> SEQ ID NO 23
<211> LENGTH: 22
<212> TYPE: PRT
<213> ORGANISM: Artificial
<220> FEATURE:
<223> OTHER INFORMATION: PAR1 partial sequence with C-terminal Cys added

<400> SEQUENCE: 23

Leu Arg Asn Pro Asn Asp Lys Tyr Glu Pro Phe Trp Glu Asp Glu Glu
1               5                   10                  15

Lys Lys Asn Glu Ser Cys
            20

<210> SEQ ID NO 24
<211> LENGTH: 31
<212> TYPE: PRT
<213> ORGANISM: Homo sapiens

<400> SEQUENCE: 24

Ala Thr Leu Asp Pro Arg Ser Phe Leu Leu Arg Asn Pro Trp Glu Asp
```

```
          1               5              10              15
Glu Glu Lys Asn Glu Ser Gly Leu Thr Glu Tyr Arg Leu Val Ser
             20              25              30
```

<210> SEQ ID NO 25
<211> LENGTH: 12
<212> TYPE: PRT
<213> ORGANISM: Homo sapiens

<400> SEQUENCE: 25

```
Ala Thr Leu Asp Pro Arg Ser Phe Leu Leu Arg Asn
1               5                  10
```

<210> SEQ ID NO 26
<211> LENGTH: 12
<212> TYPE: PRT
<213> ORGANISM: Homo sapiens

<400> SEQUENCE: 26

```
Thr Leu Asp Pro Arg Ser Phe Leu Leu Arg Asn Pro
1               5                  10
```

<210> SEQ ID NO 27
<211> LENGTH: 12
<212> TYPE: PRT
<213> ORGANISM: Homo sapiens

<400> SEQUENCE: 27

```
Leu Asp Pro Arg Ser Phe Leu Leu Arg Asn Pro Asn
1               5                  10
```

<210> SEQ ID NO 28
<211> LENGTH: 12
<212> TYPE: PRT
<213> ORGANISM: Homo sapiens

<400> SEQUENCE: 28

```
Asp Pro Arg Ser Phe Leu Leu Arg Asn Pro Asn Asp
1               5                  10
```

<210> SEQ ID NO 29
<211> LENGTH: 12
<212> TYPE: PRT
<213> ORGANISM: Homo sapiens

<400> SEQUENCE: 29

```
Pro Arg Ser Phe Leu Leu Arg Asn Pro Asn Asp Lys
1               5                  10
```

<210> SEQ ID NO 30
<211> LENGTH: 12
<212> TYPE: PRT
<213> ORGANISM: Homo sapiens

<400> SEQUENCE: 30

```
Arg Ser Phe Leu Leu Arg Asn Pro Asn Asp Lys Tyr
1               5                  10
```

<210> SEQ ID NO 31
<211> LENGTH: 12
<212> TYPE: PRT
<213> ORGANISM: Homo sapiens

<400> SEQUENCE: 31

```
Ser Phe Leu Leu Arg Asn Pro Asn Asp Lys Tyr Glu
```

```
                      1               5                  10
```

<210> SEQ ID NO 32
<211> LENGTH: 12
<212> TYPE: PRT
<213> ORGANISM: Homo sapiens

<400> SEQUENCE: 32

```
Phe Leu Leu Arg Asn Pro Asn Asp Lys Tyr Glu Pro
 1               5                  10
```

<210> SEQ ID NO 33
<211> LENGTH: 12
<212> TYPE: PRT
<213> ORGANISM: Homo sapiens

<400> SEQUENCE: 33

```
Leu Leu Arg Asn Pro Asn Asp Lys Tyr Glu Pro Phe
 1               5                  10
```

<210> SEQ ID NO 34
<211> LENGTH: 12
<212> TYPE: PRT
<213> ORGANISM: Homo sapiens

<400> SEQUENCE: 34

```
Leu Arg Asn Pro Asn Asp Lys Tyr Glu Pro Phe Trp
 1               5                  10
```

<210> SEQ ID NO 35
<211> LENGTH: 12
<212> TYPE: PRT
<213> ORGANISM: Homo sapiens

<400> SEQUENCE: 35

```
Arg Asn Pro Asn Asp Lys Tyr Glu Pro Phe Trp Glu
 1               5                  10
```

<210> SEQ ID NO 36
<211> LENGTH: 12
<212> TYPE: PRT
<213> ORGANISM: Homo sapiens

<400> SEQUENCE: 36

```
Asn Pro Asn Asp Lys Tyr Glu Pro Phe Trp Glu Asp
 1               5                  10
```

<210> SEQ ID NO 37
<211> LENGTH: 12
<212> TYPE: PRT
<213> ORGANISM: Homo sapiens

<400> SEQUENCE: 37

```
Pro Asn Asp Lys Tyr Glu Pro Phe Trp Glu Asp Glu
 1               5                  10
```

<210> SEQ ID NO 38
<211> LENGTH: 12
<212> TYPE: PRT
<213> ORGANISM: Homo sapiens

<400> SEQUENCE: 38

```
Asn Asp Lys Tyr Glu Pro Phe Trp Glu Asp Glu Glu
 1               5                  10
```

```
<210> SEQ ID NO 39
<211> LENGTH: 12
<212> TYPE: PRT
<213> ORGANISM: Homo sapiens

<400> SEQUENCE: 39

Asp Lys Tyr Glu Pro Phe Trp Glu Asp Glu Glu Lys
1               5                   10

<210> SEQ ID NO 40
<211> LENGTH: 12
<212> TYPE: PRT
<213> ORGANISM: Homo sapiens

<400> SEQUENCE: 40

Lys Tyr Glu Pro Phe Trp Glu Asp Glu Glu Lys Asn
1               5                   10

<210> SEQ ID NO 41
<211> LENGTH: 12
<212> TYPE: PRT
<213> ORGANISM: Homo sapiens

<400> SEQUENCE: 41

Tyr Glu Pro Phe Trp Glu Asp Glu Glu Lys Asn Glu
1               5                   10

<210> SEQ ID NO 42
<211> LENGTH: 12
<212> TYPE: PRT
<213> ORGANISM: Homo sapiens

<400> SEQUENCE: 42

Glu Pro Phe Trp Glu Asp Glu Glu Lys Asn Glu Ser
1               5                   10

<210> SEQ ID NO 43
<211> LENGTH: 12
<212> TYPE: PRT
<213> ORGANISM: Homo sapiens

<400> SEQUENCE: 43

Pro Phe Trp Glu Asp Glu Glu Lys Asn Glu Ser Gly
1               5                   10

<210> SEQ ID NO 44
<211> LENGTH: 12
<212> TYPE: PRT
<213> ORGANISM: Homo sapiens

<400> SEQUENCE: 44

Phe Trp Glu Asp Glu Glu Lys Asn Glu Ser Gly Leu
1               5                   10

<210> SEQ ID NO 45
<211> LENGTH: 12
<212> TYPE: PRT
<213> ORGANISM: Homo sapiens

<400> SEQUENCE: 45

Trp Glu Asp Glu Glu Lys Asn Glu Ser Gly Leu Thr
1               5                   10

<210> SEQ ID NO 46
<211> LENGTH: 12
<212> TYPE: PRT
```

```
<213> ORGANISM: Homo sapiens

<400> SEQUENCE: 46

Glu Asp Glu Glu Lys Asn Glu Ser Gly Leu Thr Glu
1               5                   10

<210> SEQ ID NO 47
<211> LENGTH: 12
<212> TYPE: PRT
<213> ORGANISM: Homo sapiens

<400> SEQUENCE: 47

Asp Glu Glu Lys Asn Glu Ser Gly Leu Thr Glu Tyr
1               5                   10

<210> SEQ ID NO 48
<211> LENGTH: 12
<212> TYPE: PRT
<213> ORGANISM: Homo sapiens

<400> SEQUENCE: 48

Glu Glu Lys Asn Glu Ser Gly Leu Thr Glu Tyr Arg
1               5                   10

<210> SEQ ID NO 49
<211> LENGTH: 12
<212> TYPE: PRT
<213> ORGANISM: Homo sapiens

<400> SEQUENCE: 49

Glu Lys Asn Glu Ser Gly Leu Thr Glu Tyr Arg Leu
1               5                   10

<210> SEQ ID NO 50
<211> LENGTH: 12
<212> TYPE: PRT
<213> ORGANISM: Homo sapiens

<400> SEQUENCE: 50

Lys Asn Glu Ser Gly Leu Thr Glu Tyr Arg Leu Val
1               5                   10

<210> SEQ ID NO 51
<211> LENGTH: 12
<212> TYPE: PRT
<213> ORGANISM: Homo sapiens

<400> SEQUENCE: 51

Asn Glu Ser Gly Leu Thr Glu Tyr Arg Leu Val Ser
1               5                   10
```